United States Patent [19]
Williams

[11] Patent Number: 4,765,731
[45] Date of Patent: Aug. 23, 1988

[54] SOLID STATE COLOR VISION TESTING SYSTEM

[75] Inventor: John M. Williams, Sunnyvale, Calif.

[73] Assignee: John J. Ferlazzo, Scarsdale, N.Y.; a part interest

[21] Appl. No.: 843,184

[22] Filed: Mar. 21, 1986

[51] Int. Cl.⁴ ............................................. A61B 3/06
[52] U.S. Cl. .................................... 351/243; 351/242; 351/246
[58] Field of Search ............... 351/242, 243, 223, 234, 351/246; 362/800

[56] References Cited

U.S. PATENT DOCUMENTS

| | | |
|---|---|---|
| 1,354,900 | 10/1920 | Frank . |
| 2,453,335 | 11/1948 | Morris . |
| 2,494,543 | 1/1950 | Clarke . |
| 3,382,025 | 5/1968 | Knoll . |
| 3,551,058 | 12/1970 | Dodds, et al. . |
| 3,807,838 | 4/1974 | Meyers . |
| 3,825,335 | 7/1974 | Reynolds . |
| 3,885,878 | 5/1975 | Ishak . |
| 3,947,099 | 3/1976 | Grolman et al. . |
| 3,981,590 | 9/1976 | Perkins . |
| 3,999,860 | 12/1976 | Demsky et al. . |
| 4,003,634 | 1/1977 | Graser, Jr. et al. . |
| 4,043,675 | 8/1977 | Guennel et al. . |
| 4,285,580 | 8/1981 | Murr . |

FOREIGN PATENT DOCUMENTS 2520604  1/1982  France ................................ 351/242

*Primary Examiner*—Rodney B. Bovernick
*Assistant Examiner*—Jay Ryan
*Attorney, Agent, or Firm*—Rohm & Monsanto

[57] ABSTRACT

A system for examining the color vision response of a human being utilizes substantially identical multicolor LEDs to function as reference and comparison color light sources. In one embodiment, the colors emitted by the LEDs are controlled by respectively associated voltage dividers. The voltage divider which cooperates with an LED to produce a reference color, is provided with a switching arrangement whereby one of a plurality of reference color compositions can be selected. The comparison color light is controlled by a voltage divider which is substantially continuously adjustable.

17 Claims, 2 Drawing Sheets

SOLID STATE COLOR VISION TESTING SYSTEM

BACKGROUND OF THE INVENTION

This invention relates generally to systems for testing color vision response in living beings, and more particularly, to a system wherein a pair of multicolored light-emitting diodes (LEDs) are used to illuminate respective portions of a bipartite visual field, one such LED being a reference color source, and the other being a comparison color source.

Color vision defects in humans are mostly hereditary and represent functional departures from the performance of the normal trichromatic eye (NTE). The NTE is called "trichromatic" because it requires, in a colorimeter an admixture of three different primary lights, in a well-defined proportion, to achieve arbitrary visible color. Four primary colors are never required in human vision, and therefore no human has a tetrachromatic eye.

If only two primary colors are required to match any arbitary visible light, the eye is considered to be colordefective and is called "dichromatic." In scotopic (night) vision, all human eyes are monochromatic, and under such conditions, lights can be recognized only by their brightness. All lights of equal brightness look alike, and no color vision exists.

Some humans have trichromatic color vision which is only slightly more discriminating than dichromatic vision, or which performs differently than what would be expected of the NTE under the same conditions. Such persons are called "anomalous trichromats" and are considered to be mildly color defective. The more serious deficiencies are red-green dichromacies and are found in approximately 3% of the male human population, and in a negligibly small percentage of the female population. The two kinds of red-green dichromacies, protanopia and deuteranopia, are held to be analogous to two corresponding anomolous trichromacies, protonomaly and deuteranomaly. Taken together, all of the red-green defects are called protan and deutan defects for brevity, and occur in approximately 10% of the male population. The tritan defects, blue-yellow deficiencies, almost never occur congenitally in either sex, but may be found occasionally in eyes which have suffered a retinal injury.

Nearly all color-vision tests concentrate on the more common red-green defects. Protanopia and deuteranopia, the most serious of the color vision defects, can be distinguished by the lower sensitivy of the protanopic eye to red light, as compared against green or yellow light under the same testing conditions. The deuteranopic eye's relative sensitivity to red, as compared to yellow or green light, usually does not differ much from that of the NTE.

The prior art is comprised essentially of two classes of color-vision testing, categorical methods and mensurative methods. Categorical methods are designed to allow the tester to count correct versus incorrect responses; the diagnosis bein made by the number and kind of incorrect responses during the test. In such known tests, booklets of color plates, such as the well known Ishihara or HRR pseudoisochromatic plates are used to display geometrical or other designs which are printed in colors in such a way as to be difficult to see or invisible to color defectives. In such tests, easier plates often are presented first so that recognition of a defect may be made at the point along the booklet at which the first error occurs. A specific diagnosis often may be made by tallying erroneous responses at the end of the test.

A further test in the categorical class, the Farnsworth-Munsell 100-Hue Test allows the testee to arrange colored chips or bits of cloth in order of their color appearance. A diagnosis is made by identifying or counting those which are not ordered correctly. Lanterns of colored light may be used to present stimuli; tbe response of the testee being to categorize the light presented.

Mensurative methods provide a measure of each response of a testee. The diagnosis of a defect is made on the basis of the high variance, or deviant mean value of several such measurements. These tests generally involve a match of two or more lights. Such matches, made by the testee are called isomeric if the spectral composition of the two correctly matched lights is identical. The matches are called metameric if, although correctly matched, they involve light with different spectral composition but the same appearance. A classical example of such a device is the Magel anomaloscope from around the turn of the century. In this well known device, a bipartite matching field is displayed with a spectral yellow light in one half-field and a mixture of spectral red and spectral green in the other. The testee adjusts the intensity of the yellow for various red and green combinations until a metameric match is obtained. A solid state analog of this well known device is described in U.S. Pat. No. 3,947,099.

The system described in the '099 patent suffers from a variety of significant disadvantages. In addition to its complexity, expense, large size, and relatively high weight, the known arrangement requires, in its preferred form, correlated adjustment of the red-green mixture, making difficult the study of a matching as a function of red plus green intensity. Thus, optics are required to create a matching field. The known arrangement further requires at least three separate diode sources for red, green, and yellow light, each such source being vulnerable to calibration drift independently of each other. Only one yellow standard light is provided, thereby requiring prolonged testing to separate protan from deutan defects. Additionally, the known arrangement does not permit isomeric matching of the two half-fields, thereby excluding, or rendering very difficult, a strictly instrumental calibration of the matching point. Finally, the known arrangement utilizes a bipartite field formed of fiber optics which will be grainy in appearance and must have either a thick blocked-off line or an irregular line dividing the two halves of the field. It is well known that the less salient the edge between matching fields, the more accurate the testee's match. Also, with such fiber optics, each broken fiber in the bundle creates a black spot in the field, and large bundles of such optical fibers are difficult and expensive to fabricate with zero breakage.

It is, therefore, an object of this invention to provide a simple and inexpensive system for testing color vision response.

It is another object of this invention to provide a color vision testing system which is highly portable.

It is a further object of this invention to provide a color vision testing system wherein the LEDs whlch provide the multiple color outputs are very stable and have junction temperatures which change substantially simultaneously.

It is also an object of this invention to provide a color vision testing system which does not require optics.

It is an additional object of this invention to provide a color vision testing system which can be calibrated easily using a spectrometer.

It is a still further object of this invention to provide a system for testing color response which can produce a plurality of predetermined reference light colors.

It is still another object of this invention to provide a color vision testing system wherein an isomeric match can be achieved by a testee.

SUMMARY OF THE INVENTION

The foregoing and other objects are achieved by this invention which provides in an apparatus aspect thereof an arrangement for testing color vision response having first and second LEDs each having an electrical input for receiving an associated electrical input signal and an associated optical output from which is emitted an output optical signal. The output optical signal has a color composition characteristic which is responsive to the electrical input signal. The arrangement is further provided with an electrical supply which delivers to the first and second LEDs a cyclically varying electrical input. Each such LED has associated therewith one of first and second signal control arrangements for controlling the color composition of the output optical signals.

In one embodiment, an electrical coupling arrangement is provided whereby the LEDs and their respectively associated control systems are reversed. Thus prior to actuation of the selectable coupling arrangement, a first coupling state is in effect in which the first LED is coupled to the first signal control arrangement and the second LED is coupled to the second control arrangement. Upon actuation of the selectable coupling a second coupling state is effected in which the first LED is coupled to the second signal control system and the second LED is coupled to the first signal control system.

In accordance with a further embodiment of the invention, each LED has associated therewith a respective one of first and second illuminated members which are arranged in the vicinity of the optical output. In a practical embodiment, the first and second illuminated members are arranged substantially adjacent to one another so as to form a bipartite visual field. Preferably, the illuminated members are formed integrally with a shield which is rolled around the associated LED so as to prevent undesired scattering of the light emitted by the LED.

In accordance with the invention, the LEDs are each of the type which are provided with at least two light generating members, each such light generating member being adapted to produce a different color output light. In a preferred embodiment, one such light generating member may emit a green light, while the other may emit a red light. Each LED package therefore contains two internal light generating members which may themselves be light emitting diodes, and which are poled for conduction in opposite directions. Thus, in an illustrative embodiment of the invention, conduction of the current in a first direction through the LED may generate a green light output, while reverse conduction may produce a red light. An alternating signal is applied wherein current through the LED alternates rapidly so as to flow in both directions, the result will be a yellow light which is formed as a composite of the green and red lights.

In the practice of the invention, one of the LEDs is used to emit a reference color, and the other emits a comparison color. The reference color LED is controlled by a voltage divider arrangement having a switch which is actuatable to select one of several reference colors. The comparison LED is controlled by a further voltage divider arrangement which is provided with a substantially continuously variable element, such as a potentiometer which permits the comparison output light to be varied in color. The color of the output light from each LED is determined, in such an embodiment, by adjusting the voltage divider which in turn determines whether the light from the red half cycle or the green half cycle of a cyclically varying supply will have the greater intensity in the mixture. In a preferred specific embodiment, the supply contains timing circuitry, such as a well known 555 timer chip, which produces at its output a square wave having a frequency of approximately 1.2 KHz. A light pulsating at 1.2 KHz cannot be differentiated from a steady light by anything in the human visual system beyond the matrix of the visual photo pigment itself. The square wave voltage is dropped across both LEDs in this embodiment, each of which is in series with the mid-point of the aforementioned associated voltage divider. In practice, the voltage divider is formed of precision resistors. It is to be understood that variations in the output colors of the LEDs can be achieved not only by adjustment of the respective voltage dividers, but also by adjusting the duty cycle of the cyclically varying supply.

In accordance with a method aspect of the invention, a color composition of the light output of a multicolored LED is controlled to produce a reference color composition and a first portion of a visual field. The color composition of the light output of the second multicolor LED is controlled to produce a comparison color composition on a second portion of the visual field.

In addition to being light in weight, small and easily transportable, and inexpensive, it is a significant advantage of the present invention that optics are not required in the practice of the invention. However, an eyepiece may be provided to enlarge the visual field. Moreover, the system of the present invention can easily be interfaced with electronic monitoring or recording equipment.

BRIEF DESCRIPTION OF THE DRAWING

Comprehension of the invention is facilitated by reading the following detailed description in conjunction with the annexed drawing, in which.

DETAILED DESCRIPTION

Figure 1:
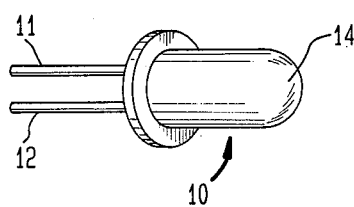
FIG. 1 is an isometric representation of an LED suitable for use in the practice of the invention.

FIG. 1 is an isometric representation of an LED 10 having an electrical input formed of leads 11 and 12. The LED is further provided with a lens 14 through which is emitted a light having a color composition and intensity responsive to an electrical signal applied at lead 11 and 12. As will be discribed hereinbelow with respect to FIG. 7, LED 10 is a multicolor LED. The color of the light which is emitted through lens 14 at any given instant of time is a function of the direction of current flow through leads 11 and 12. In this specific illustrative embodiment, LED 10 is of the type whicb emits a green light when conventional current flows into lead 11 and out through lead 12, and a red light when the current flows through lead 12 and out through lead 11. Also as will be described hereinbelow, the color of the light emitted through lens 14 can be a composite of red and green depending upon the characteristics of the electrical input signals.

Figure 2:
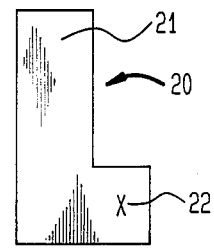
FIG. 2 is a plan view of a specific illustrative embodiment of a shield suitable for controlling the output light LED of FIG. 1.

FIG. 2 is a plan view of a shield 20 having a shielding portion 21 and an illuminated portion 22. As shown in this figure, illuminated portion 22 is identified with an x for the purpose of facilitating visualization and understanding of FIG. 3. However, in practice, the x will not be apparent on the illuminated portion.

Figure 3:
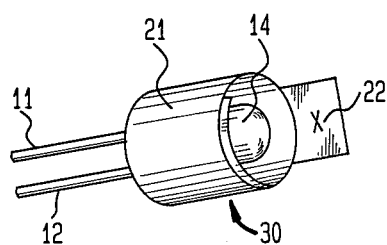
FIG. 3 is an isometric representation of the LED of FIG. 1 with the shield of FIG. 2 arranged thereon.

FIG. 3 is an isometric representation of a shielded LED assembly 30 which is formed of LED 10 having shielding portion 21 of shield 20 wrapped therearound, As shown, illuminated portion 22 of the shield is shown to extend outward from shielding portion 21 and in a position to be illuminated by the light which is emitted from lens 14.

Figure 4:
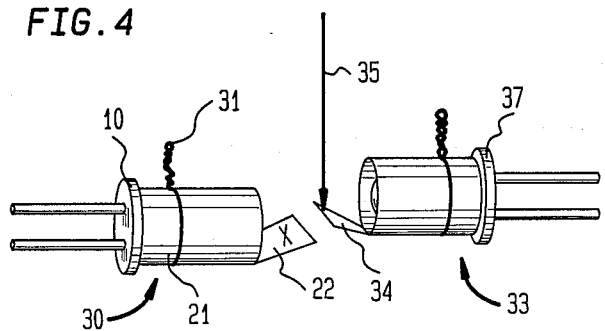
FIG. 4 shows two LEDs with shields installed thereon in the process of being brought into communication with one another.

FIG. 4 is a side view of shielded LED array 30 and a further LED array 33. In this embodiment, the shielded LED arrays have been provided with a length of thin wire wrapped therearound, such as wire 31 which insures that shielded portion 21 of tbe shield remains securely around the LED. As shown in this figure, an illuminated portion 34 of shielded LED assembly 43 is brought into communication with illuminated portion 22 of shielded LED assembly 30. Arrow 35 designates the visual axis of the testee.

Figure 5:
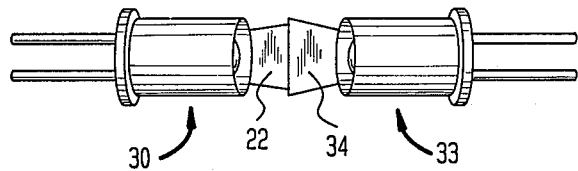
FIG. 5 is a top plan view of the arrangement of FIG. 4 showing the relationship between the illuminated portion of the respective shields.

FIG. 5 shows shielded LED assembly 30 and 33 from the top so that a bipartite field is seen to be produced by illuminated portions 22 and 34. In the practice of the present invention, the shield can be formed of a heavy white paper, such as index card paper. Preferably, the twisted wire, as shown in FIG. 4, is twisted so as to secure the shields to the LEDs after telescoping and adjusting the wrapped tube formed of shielded portion 21 so as to insure tbat the illuminated portions are evenly illuminated. After the adjustments are completed, the entire assembly, except the illuminated portion 22 and 34, are painted, in this embodiment, white, and then black hobbyist's enamel.

The arrangement of FIG. 5 is installed into a small cell (not shown) so as to form a small light box. There is, however, provided a small clrcular opening as shown in FIG. 6.

Figure 6:
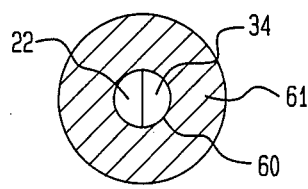
FIG. 6 is a view of a bipartite visual field.
Figure 7:
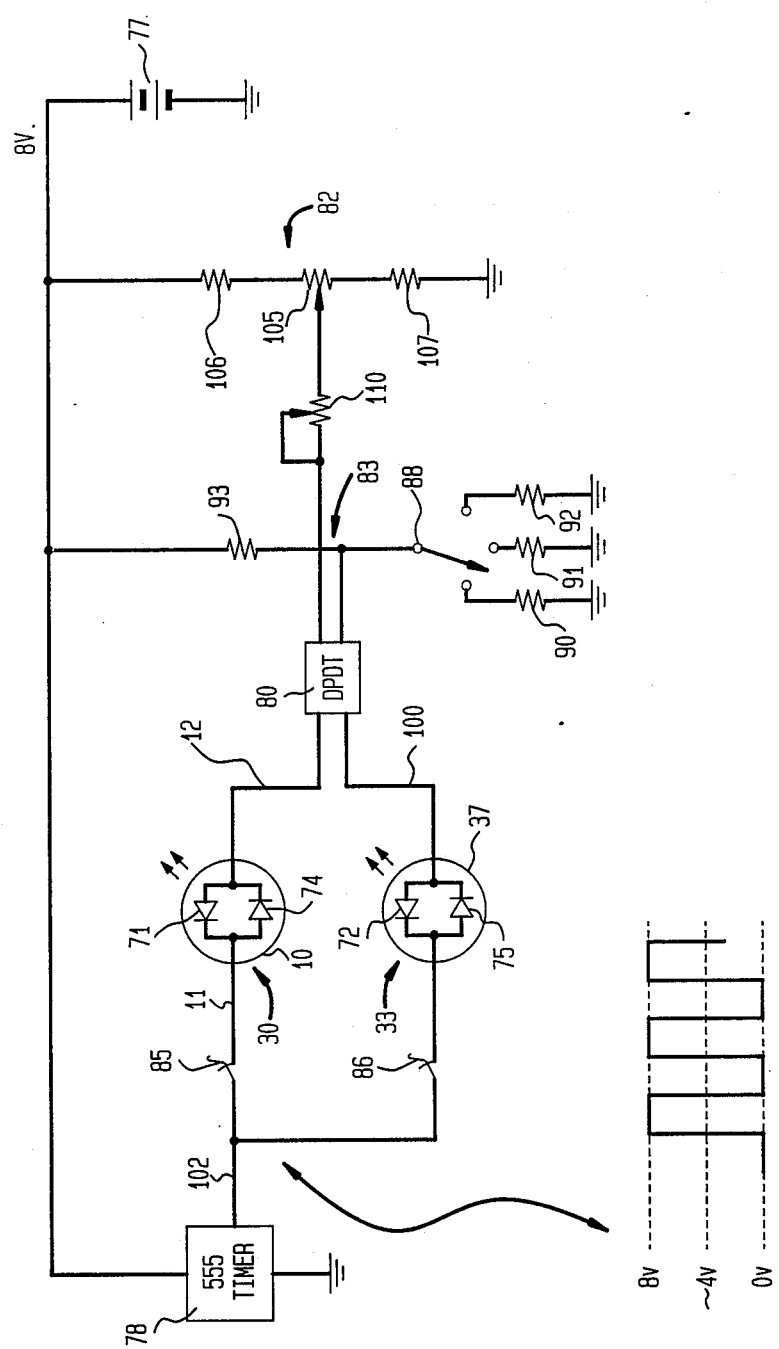
FIG. 7 is a schematic and block and line representation of energizing and control circuitry.

FIG. 6 shows an opening 60 through which is visible illuminated portions 22 and 34. An area 61 surrounding opening 60 is printed black in this embodiment. A piece of clear glass (not shown) can be provided to close opening 60 while retaining visibility of the illuminated portion. In this manner, the LEDs, their respective shields, and the circuitry which will be described hereinbelow can be sealed within the cell, if desired. The invention can be used to test for color vision defects without the need for optics. However, an optional eyepiece (not shown) can be provided to enlarge the field of view. Proper alignment of the illuminated portion, and beveled cutting, permits the border between them almost to vanish when a color match is achieved, FIG. 7 is a schematic and block and line representation of a specific illustrative embodiment of the invention. Shielded LED assemblies 30 and 33 are shown in schematic form and contain LEDs 10 and 37 which are identical to one another. Each such LED is provided with a red light emitting element 71 and 72, and a green light emitting element 74 and 75. As shown, the LEDs are excited by a nominal 1.2 KHz square wave voltage obtained from a battery 77 and a switching element 78. Switching element 78 may be a standard, commercially-available 555 timer integrated circuit. The square wave voltage is dropped across both LEDs, each of which is in series with the mid-point of a respectively associated precision resistor voltage divider. The series connection, however, is subject to a double pole double throw switch 80 which is connected to permit the coupling of the LEDs to the voltage dividers to be reversed.

For the purposes of facilitating the description herein, lead 12 of LED 10 is coupled to a voltage divider 82, while LED 37 is connected to voltage divider circuit 83. However, it is understood that actuation of switch 80, which is cross-connected in a known manner, would result in reversal of the connections between the LEDs and the voltage divider circuits. The voltage divider for each LED determines whether the light from the red half-cycle or the green half-cycle will have the greater intensity in the mixture. The component of current flowing to each LED can be monitored, in this embodiment, by an associated one of panel jacks 85 and 86.

Assuming that double pole double throw switch 80 is in the fixed position indicated hereinabove, LED 37 will be the reference LED, and LED 10 will be the comparison LED. With respect to the reference LED, one of three reference colors can be selected, in this embodiment, by actuation of switch 88. Switch 88 selects one of resistors 90, 91, or 92 to complete a voltage divider circuit with resistor 93. For example, the reference colors associated witb the resistors 90, 91, and 92 may respectively be too greenish to be seen as yellow by the NTE, too reddish to be seen as yellow by the NTE, or clearly a yellow to the NTE. Voltage divider network 83 determines the nominal DC voltage present at lead 100 connected to LED 37 as a function of the selected resistor. Such a selection also determines the voltage at which the current flowing through the LED will be reversed. For example, assuming that resistors 93 and 90 have equal value, then lead 100 will be at 4 Volts with respect to ground, since, in this embodiment, battery 77 produces 8 Volts. Thus, when the square wave energizing signal at output lead 102 of switching element 78 is at 8 volts, current flows through the lead 102 toward ground at one end of resistor 90. However, when the square wave energizing signal is at zero volts, current then flows through resistor 93 and into switching element 78 which, at that time, provides a ground current path.

LED 10, functioning as the reference LED, is operated in a manner simlar to that described herein. However, the point at which current flowing through the reference LED is reversed is set by the position of a potentiometer 10t in voltage divider 82. This voltage divider, which is formed of resistors 106, 107, and potentiometer 105, is further provided with an intensity control in the form of a variable resistor 110. After a test has been completed by manipulating potentiometer 105 to achieve a color match between the LEDs, double pole double throw switch 80 may then be actuated to allow a functional reversal of position of the field, as viewed by the testee. This feature permits counterbalanced circuit calibration and flexibility in presenting the problem to the testee.

Although the invention has been disclosed in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the inveniton and should not be construed to limit the scope thereof.

What is claimed is:

1. An arrangement for testing color vision response, the arrangement comprising:
    first and second LED means, each having an electrical input for receiving an associated one of first and second electrical input signals and an associated optical output from which is emitted an output optical signal having a color composition responsive to said associated one of said first and second electrical input signals;
    electrical supply means coupled to said electrical inputs of said first and second LED means for delivering thereto a cyclically varying electrical energy having a substantially constant duty cycle; and
    first and second control means for controlling respective ones of said electrical input signals and said color composition of said output optical signals.

2. The arrangement of claim 1 wherein there is further provided selectable coupling means having a first coupling state wherein said first LED is coupled to said first signal control means and said second LED is coupled to said second signal control means, and a second coupling state wherein said first LED is coupled to said second signal control means, and said second LED is coupled to said first signal control means.

3. The arrangement of claim 1 wherein there are further provided first and second illuminated members arranged in the vicinity of said optical outputs of said first and second LED means.

4. The arrangement of claim 3 wherein said first and second illuminated members are arranged substantially adjacent to each other to form a bipartite field.

5. The arrangement of claim 4 wherein there is further provided means for defining an outermost extent of said bipartite field.

6. The arrangment of claim 4 wherein there is further provided optical means for optically enlarging said bipartite field.

7. The arrangement of claim 1 wherein said first and second LED means are each provided with first and second light generating members, each such light generating member being adapted to produce a different color output light.

8. The arrangement of claim 7 wherein said first and second signal control means each comprise a voltage divider means whereby a proportion of electrical currents flowing through said light generating members of an associated LED means is adjustable to obtain a selectable mixture of said color output light.

9. The arrangement of claim 1 wherein said electrical supply means comprises switching means for producing said cyclical variations in said electrical energy.

10. The arrangement of claim 9 wherein said switchin means has an adjustable duty cycle for controlling at least partially said color composition.

11. A method of subjecting a living being to an examination of visual color response, the method comprising:
    first controlling a switchable resistive voltage divider for controlling a color composition of a light output of a first multicolor LED to produce a selectable one of a plurality of predetermined reference color compositions on a first portion of a visual field; and
    second controlling a continuously variable resistive voltage divided for controlling a color composition of a light output of a second multicolor LED to produce a comparison color composition on a second portion of said visual field.

12. The method of claim 11 wherein said first and second multicolor LEDs each emit a respectively selectable combination of red and green output light.

13. The method of claim 11 wherein said step of second controlling comprises the further step of varying said comparison color composition on said second portion of said visual field substantially continuously.

14. The method of claim 11 wherein there is further provided the further step of reversing said first and second portions of said visual field whereby, upon completing said step of reversing, said step of first controlling controls said second multicolor LED and said step of second controlling controls and said first multicolor LED.

15. A system for testing color vision response, the system comprising:
    a reference multicolor light source for illuminating a reference portion of a visual field;
    reference control means for controlling a reference color composition of said illumination of said reference portion to select one of a plurality of selectable reference color compositions;
    a comparison multicolor light source for illuminating a comparison portion of a visual field;
    comparison control means for controlling a comparison color composition of said illumination of said comparison portion continuously over a predetermined range of color compositions;
    first and second cover means each associated with a respective one of said reference and comparison multicolor light sources, each of said cover means having an illuminated portion arranged in the visual field, said illuminated portion of said first cover means being arranged in said reference portion of the visual field, and said illuminated portion of said second cover means being arranged in said comparison portion of said visual field.

16. The system of claim 15 wherein said reference control means comprises reference voltage divider means having selectable resistor means for selecting one of a plurality of said selectable reference color compositions.

17. The system of claim 15 wherein said comparison control means comprises comparison voltage divider means having substantially continuous variable resistor means for varying said comparison color composition.

* * * * *